(12) United States Patent
Anvari

(10) Patent No.: US 7,979,157 B2
(45) Date of Patent: Jul. 12, 2011

(54) MULTI-PURPOSE ROBOTIC OPERATING SYSTEM AND METHOD

(75) Inventor: Mehran Anvari, Hamilton (CA)

(73) Assignee: McMaster University, Hamilton, ON (CA)

( * ) Notice: Subject to any disclaimer, the term of this patent is extended or adjusted under 35 U.S.C. 154(b) by 985 days.

(21) Appl. No.: 11/187,889

(22) Filed: Jul. 25, 2005

(65) Prior Publication Data

US 2006/0149418 A1 Jul. 6, 2006

Related U.S. Application Data

(60) Provisional application No. 60/590,416, filed on Jul. 23, 2004.

(51) Int. Cl.
*G06F 19/00* (2011.01)

(52) U.S. Cl. ........ 700/245; 700/247; 700/248; 700/249; 700/251; 700/253; 700/257

(58) Field of Classification Search .......... 414/266–286, 414/498–559, 595–605; 700/245–264
See application file for complete search history.

(56) References Cited

U.S. PATENT DOCUMENTS

| | | | |
|---|---|---|---|
| 4,638,231 A | 1/1987 | Monforte | 318/640 |
| 4,644,237 A | 2/1987 | Frushour et al. | 318/313 |
| 4,729,536 A * | 3/1988 | Scala | 248/429 |
| 5,485,995 A | 1/1996 | Newgarden, Jr. | 273/30 |
| 5,555,897 A | 9/1996 | Lathrop et al. | 128/845 |
| 5,668,452 A | 9/1997 | Villarreal et al. | 318/568.16 |
| 5,790,996 A | 8/1998 | Narfstrom | 5/610 |

(Continued)

FOREIGN PATENT DOCUMENTS

JP 4146097 5/1992

OTHER PUBLICATIONS

Bowersox et al, "Use of Intiuitive Telemanipulator System for Remote Trauma Surgery: An Experimental Study", J. Am Coll Surg, vol. 186, No. 6 Jun. 1998: 6-5-621.

(Continued)

*Primary Examiner* — Khoi Tran
*Assistant Examiner* — Bhavesh V Amin

(57) ABSTRACT

A dynamically configurable robotic system and method for performing surgical operations using a plurality of robotic arms remotely controlled by at least one operator console. The system comprises a track system configured for mounting to a patient support table, such that the track system provides a stable operating platform for the robotic arms and for facilitating placement of a proximal end of each of the arms at a selected position about a periphery of the patient support table. the system and method also have a plurality of base stations for operatively coupling each of the robotic arms to the track system, such that each of the base stations include a housing, a first connector for coupling the housing to the track system, the first connector configured for facilitating movement of the housing along the track system while coupled thereto, and a second connector for coupling the housing to the proximal end of at least one of the robotic arms, the second connector configured for providing at least one of power supply, control signalling, and data communication with respect to the coupled robotic arm. The system and method also have a control unit for coupling to at least two of the base stations and configured for dynamically connecting operative remote control between the coupled base stations and a first operator console of the at least one operator console.

27 Claims, 11 Drawing Sheets

U.S. PATENT DOCUMENTS

| | | | |
|---|---|---|---|
| 5,911,036 A | 6/1999 | Wright et al. | 395/94 |
| 6,102,850 A | 8/2000 | Wang et al. | 600/102 |
| 6,195,578 B1 | 2/2001 | Distler et al. | 600/415 |
| 6,262,863 B1 * | 7/2001 | Ostwald et al. | 360/92.1 |
| 6,330,493 B1 * | 12/2001 | Takahashi et al. | 700/245 |
| 6,441,577 B2 | 8/2002 | Blumenkranz et al. | 318/568.11 |
| 6,456,684 B1 | 9/2002 | Mun et al. | 378/20 |
| 6,804,581 B2 * | 10/2004 | Wang et al. | 700/251 |
| 2002/0038118 A1 | 3/2002 | Shoham | 606/1 |
| 2002/0082612 A1 | 6/2002 | Moll | 606/130 |
| 2002/0091374 A1 | 7/2002 | Cooper | 606/1 |
| 2002/0111713 A1 | 8/2002 | Wang et al. | 700/245 |
| 2002/0128633 A1 | 9/2002 | Brock et al. | 606/1 |
| 2003/0013949 A1 | 1/2003 | Moll et al. | 600/407 |
| 2003/0109780 A1 * | 6/2003 | Coste-Maniere et al. | 600/407 |
| 2003/0176948 A1 | 9/2003 | Green | 700/264 |
| 2003/0180697 A1 | 9/2003 | Kim et al. | 434/219 |

OTHER PUBLICATIONS

Schurr et al, "Robotics and telemanipulation technologies for endoscopic surgery; A review of the ARTEMIS project" Surgical Endoscopy, (2000) 14: 375-381.

* cited by examiner

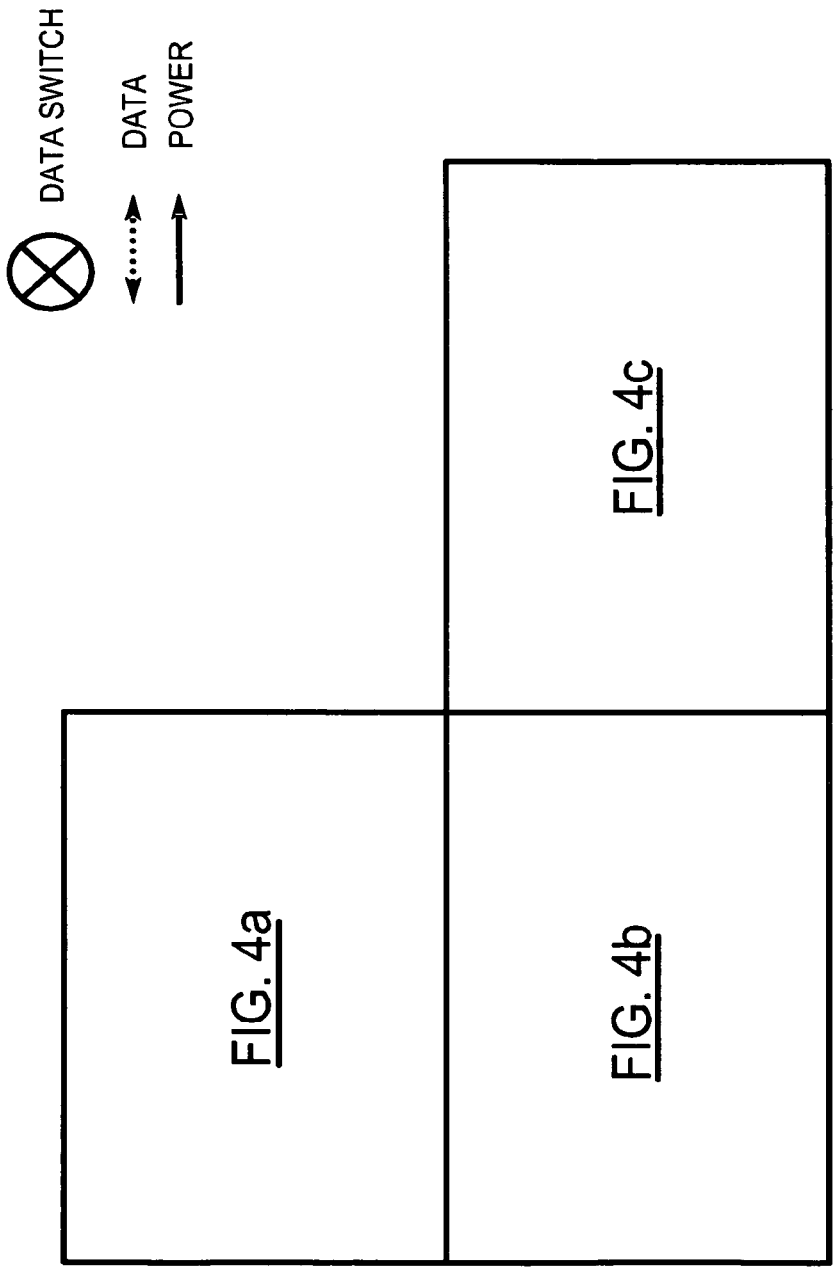

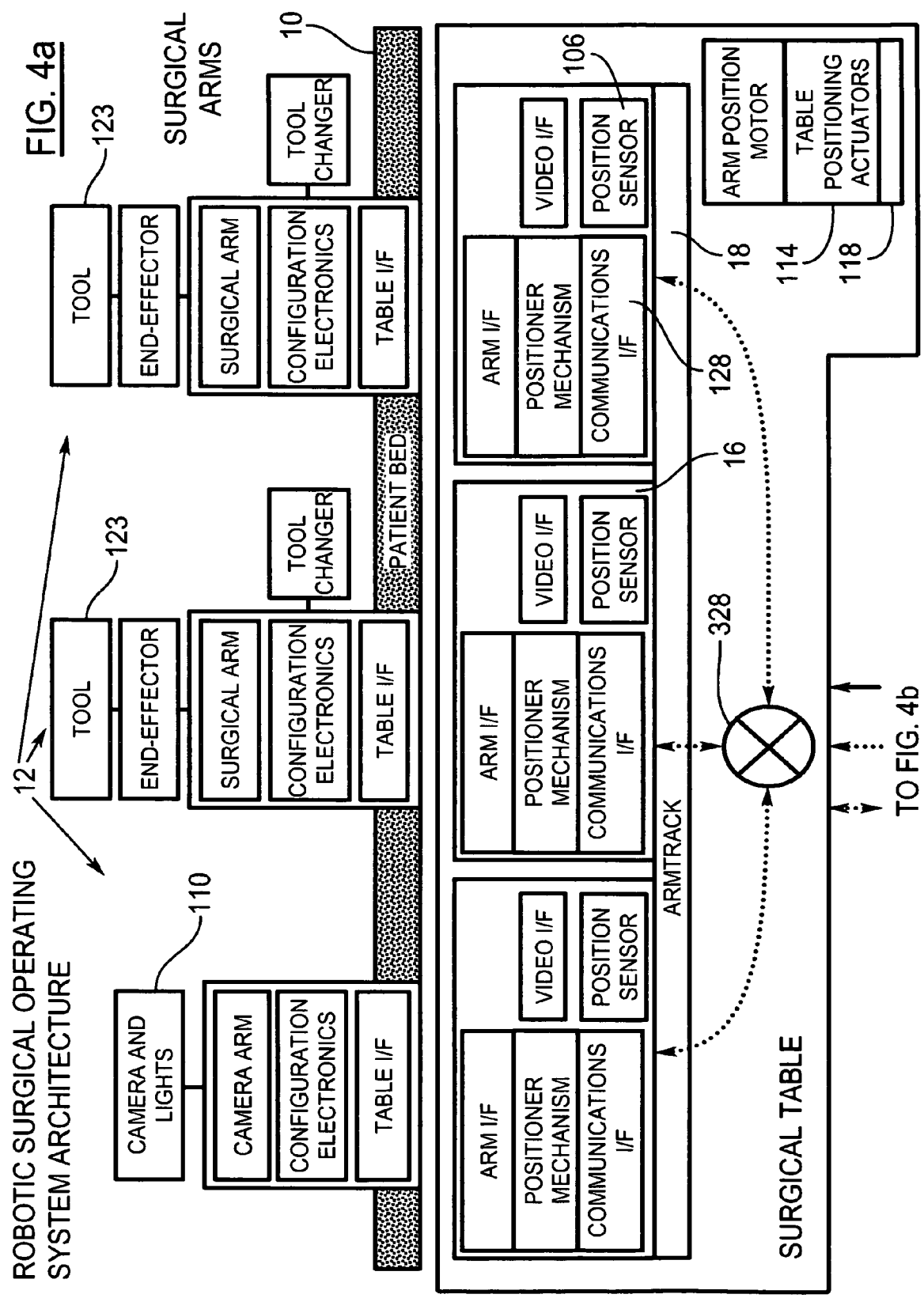

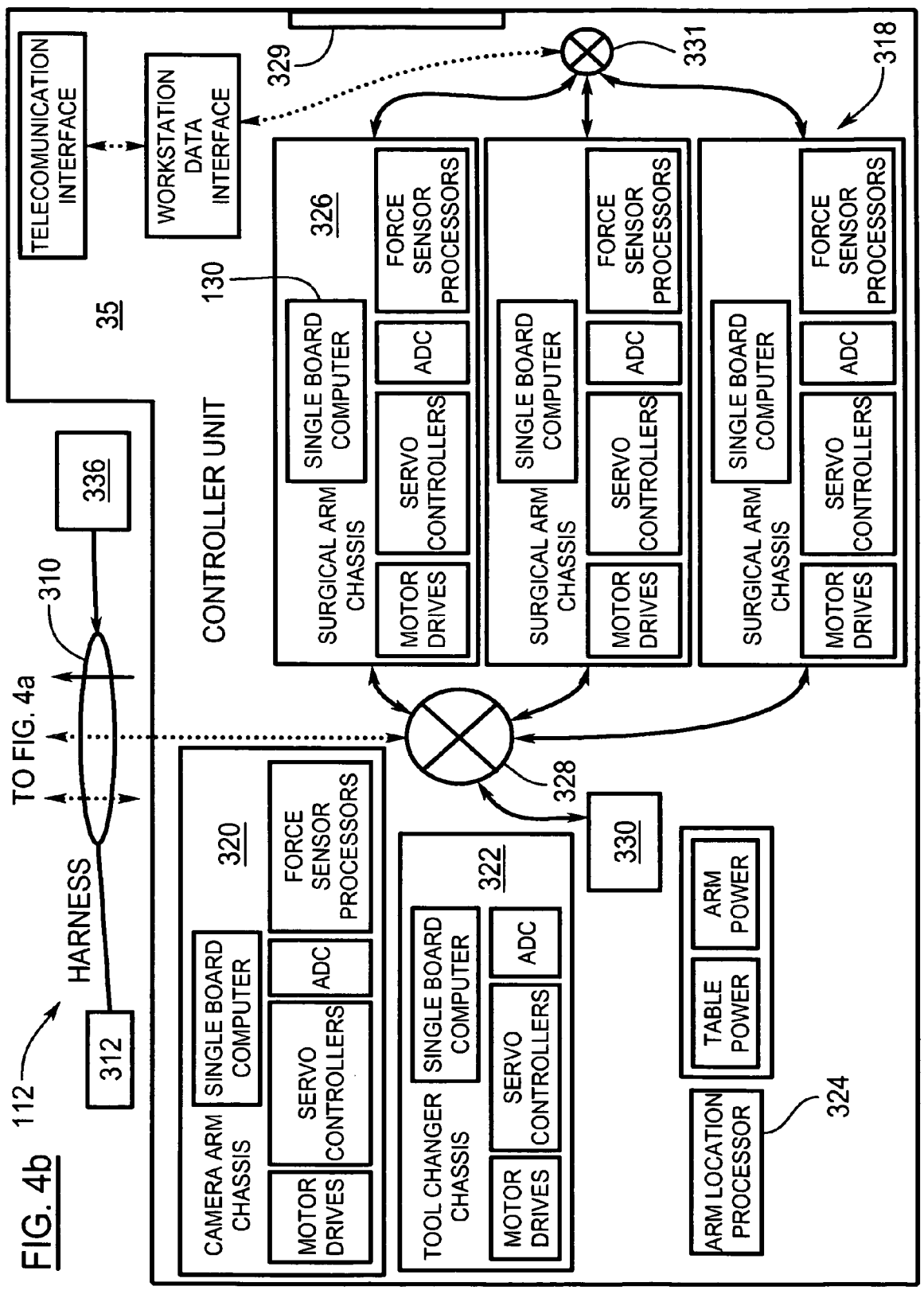

MULTI-PURPOSE ROBOTIC OPERATING SYSTEM AND METHOD (This application claims priority from U.S. Provisional Application No. 60/590,416, filed on Jul. 23, 2004.)

The present invention relates to robotically-assisted surgical manipulators and more particularly to systems and methods for performing telerobotic surgical procedures.

BACKGROUND OF THE INVENTION

In robotically-assisted or telerobotic surgery, the surgeon typically operates a master controller to remotely control the motion of surgical instruments affixed to robotic arms positioned at the surgical site. The master controller is in a location that may be remote from the patient (e.g., across the operating room, in a different room or a completely different building from the patient). The master controller usually includes one or more hand input devices, which are coupled to the robotic arms holding the surgical instruments, and the master controller controls servo motors associated with the robotic arms for articulating the instruments at the surgical site. During the operation, the hand devices provide mechanical articulation and control of a variety of surgical instruments, coupled to the robotic arms, that each perform various surgical functions for the surgeon.

Current surgical robotic systems comprise either robot arms fastened to the side of an operating table at fixed locations or a robot arm fastened to a separate movable stand that can be positioned adjacent to the operating table. Disadvantages for current systems include complex manual setup procedures and undesirably long setup times prior to surgery, as well as the cable requirements to couple the robotic arms to the master controller. The presence of cabling can interfere with the movement of assistants about the operating table. For example, for current systems, placement of the table (and secured patient) within an imaging device is problematic while the robot arms are attached. Another disadvantage of current systems is that they are restricted to performing specific classes of surgical procedures for example laparoscopic operations and a different class necessitates another type of robotic system. For multiple surgical tasks in a specified region of the patient, current systems can require the undesirable manual repositioning and/or substitution of a replacement robotic system while the patient is resident on the table. Further disadvantages with current systems can include the need for re-registration and time consuming cable routing and robot positioning.

SUMMARY OF THE INVENTION

It is an object of the present invention to provide a multi-purpose robotic operating system and method to obviate or mitigate at least some of the above presented disadvantages.

Disadvantages for current systems include complex manual setup procedures and undesirably long setup times prior to surgery, as well as the cable requirements to couple the robotic arms to the master controller. A further disadvantage of current systems is that robot arms are difficult to sterilize and can be undesirably bulky adjacent to the operating table, thereby interfering with movement of the table while the robot arms are attached. Another disadvantage of current systems is that they are restricted to performing specific classes of surgical procedures for example laparoscopic operations and a different class necessitates another type of robotic system. For multiple surgical tasks in a specified region of the patient, current systems can require the undesirable manual repositioning and/or substitution of a replacement robotic system while the patient is resident on the table. Contrary to current robotic systems there is provided a dynamically configurable robotic system and method for performing surgical operations using a plurality of robotic arms remotely controlled by at least one operator console. The system comprises a track system configured for mounting to a patient support table, such that the track system provides a stable operating platform for the robotic arms and for facilitating placement of a proximal end of each of the arms at a selected position about a periphery of the patient support table. the system and method also have a plurality of base stations for operatively coupling each of the robotic arms to the track system, such that each of the base stations include a housing, a first connector for coupling the housing to the track system, the first connector configured for facilitating movement of the housing along the track system while coupled thereto, and a second connector for coupling the housing to the proximal end of at least one of the robotic arms, the second connector configured for providing at least one of power supply, control signalling, and data communication with respect to the coupled robotic arm. The system and method also have a control unit for coupling to at least two of the base stations and configured for dynamically connecting operative remote control between the coupled base stations and a first operator console of the at least one operator console.

A first aspect provided is a dynamically configurable robotic system for performing surgical operations using a plurality of robotic arms remotely controlled by at least one operator console, the system comprising: a track system configured for mounting to a patient support table, the track system for providing a stable operating platform for the robotic arms and for facilitating placement of a proximal end of each of the arms at a selected position about a periphery of the patient support table; a plurality of base stations for operatively coupling each of the robotic arms to the track system, each of the base stations including a housing, a first connector for coupling the housing to the track system, the first connector configured for facilitating movement of the housing along the track system while coupled thereto, and a second connector for coupling the housing to the proximal end of at least one of the robotic arms, the second connector configured for providing at least one of power supply, control signalling, and data communication with respect to the coupled robotic arm; and a control unit for coupling to at least two of the base stations and configured for dynamically connecting operative remote control between the coupled base stations and a first operator console of the at least one operator console.

A second aspect provided is a method for dynamically configuring a robotic system to perform surgical operations using a plurality of robotic arms remotely controlled by at least one operator console, the method comprising the steps of: coupling a control unit to at least two selected base stations of a plurality of base stations, the selected base stations connected to selected robotic arms of the plurality of robotic arms, the control unit configured for dynamically connecting operative remote control between the selected base stations and a first operator console of the at least one operator console; and recording the position of each of the selected base stations at respective locations along a track system mounted to a patient support table, the selected base stations for operatively coupling each of the selected robotic arms to the track system, each of the selected base stations including a housing, a first connector for coupling the housing to the track system, the first connector configured for facilitating movement of the housing along the track system while coupled thereto, and a second connector for coupling the housing to the proximal end of at least one of the selected robotic arms, the second connector configured for providing at least one of power supply, control signalling, and data communication with respect to the selected robotic arm; wherein the track system provides a stable operating platform for the selected robotic arms and facilitates placement of a proximal end of each of the selected robotic arms at the respective locations about a periphery of the patient support table.

A third aspect provided is a dynamically configurable robotic system for performing surgical operations using at least one robotic arm remotely controlled by at least one operator console, the system comprising: a track system configured for mounting to a patient support table, the track system for providing a stable operating platform for the at least one robotic arm and for facilitating placement of a proximal end of the at least one robotic arm at a selected position about a periphery of the patient support table; a base station for operatively coupling the at least one robotic arm to the track system, the base station including a housing, a first connector for coupling the housing to the track system, the first connector configured for facilitating movement of the housing along the track system while coupled thereto, and a second connector for coupling the housing to the proximal end of the least one robotic arm, the second connector configured for providing at least one of power supply, control signalling, and data communication with respect to the coupled robotic arm; and a control unit for coupling to the base station and configured for dynamically connecting operative remote control between the coupled base station and a first operator console of the at least one operator console.

BRIEF DESCRIPTION OF THE DRAWINGS

These and other features of the preferred embodiments of the invention will become more apparent in the following detailed description in which reference is made to the appended drawings by way of example only, wherein.

DESCRIPTION OF THE PREFERRED EMBODIMENTS

Figure 1:
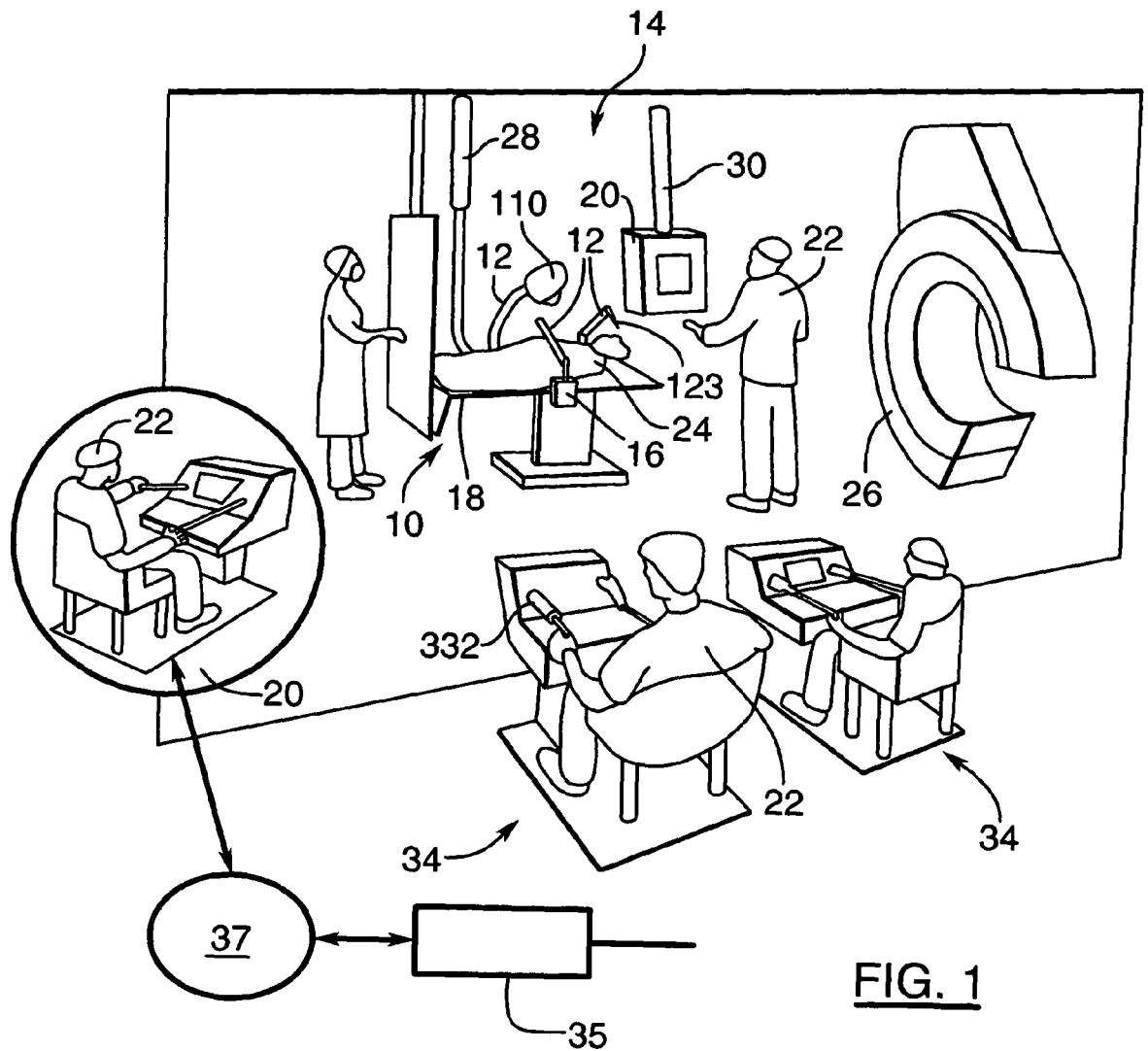
FIG. 1 is a view of a multipurpose robotic operating system.
Figure 4C:
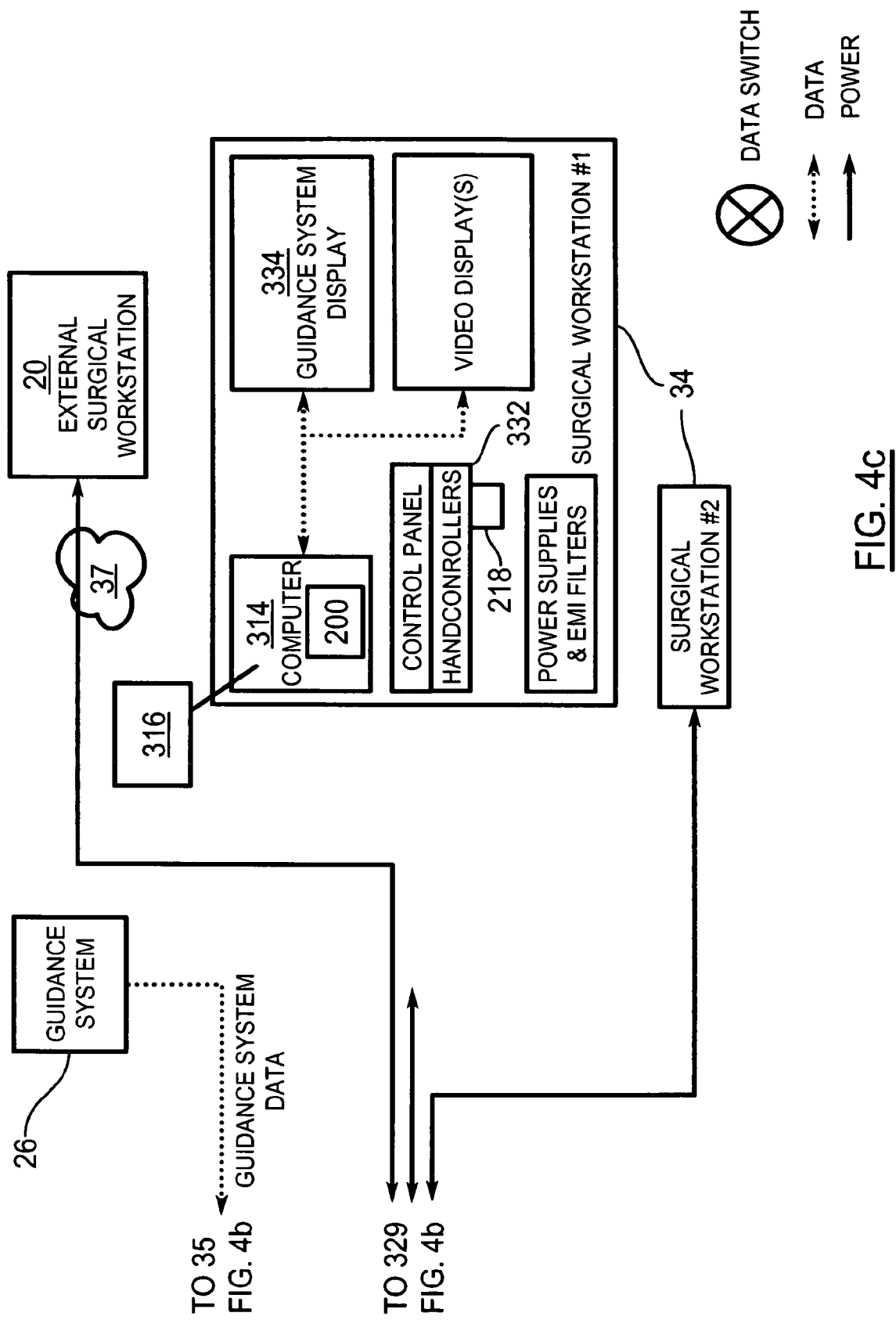
FIG. 4 is a functional block diagram of the system of FIG. 1.

Referring to FIG. 1, an operating bed or table 10 incorporating up to, for example, eight flexible robotic arms or manipulators 12 is shown in an operating room 14. Each of the arms 12 is releasably secured to a respective base station 16 which can travel along a track system 18 positioned at the side of the table 10. It is noted that the base stations 16 are securely mounted to the track system 18, such that the base stations 16 can be remotely controlled by a console 20,34 via hand controllers 332 (see FIG. 4) to reposition the base stations 16 at various locations along the rails of the track system 18 (as specified by an operator 22 of the console 20,34). Each arm 12 is attached to its respective base station 16 such that the arm 12 and/or base station 16 can be retracted or otherwise folded down and out of the way to the side or underneath the table 10, if not required for the surgical procedure being performed. Relative position and orientation of the base stations 16 and associated arms 12 are monitored by software 200 (see FIG. 4) of the consoles 20,34, with respect to a common reference coordinate system 60 (e.g. room 14 coordinate system, table 10 coordinate system, patient 24 coordinate system where patient position trackers are used, etc. . . . ), see FIG. 2. Preferably, the immediate physical space that the robot arms 12 occupies could be as small as possible, such that the arms 12 are possibly stored beneath the table 10 to minimize the arms 12 footprint, while remaining attached to the base stations 16, if desired. Further, the base stations 16 and/or arms 12 preferably can be retracted to a convenient position under the table 10 so as to accommodate movement of the table 10 and resident patient 24 in respect to an imaging apparatus 26. The arms 12 can have six degrees of freedom and can enable robotic surgery by the operator 22 in cooperation with real time radiological evaluations by either, for example, CT, MRI or fluoroscopy imaging apparatus 26. Further, it is recognised that the selectable position capability of the base stations 16 on the track system 18 adds another motion degree-of-freedom to each arm 12 that can be used by a controller unit 35 (see FIG. 4) to increase the workspace of the arm 12 and/or maintain the distal arm 12 position/orientation while moving the arm 12 out of the way of other arms 12 or another device 38 (e.g. fluoroscopic imager 110).

Further, the operating room table 10 would contain electrical and mechanical interfaces 120a,b,c 121a,b,c (see FIG. 3) for several surgical robotic manipulators or arms 12. The arms 12 are remotely controlled using the console 20,34 (e.g. surgical workstation) preferably located away from the table 10, such as but not limited to within a hospital as connected to a hospital local network 31 (see FIG. 4) and/or a remote network 37 such as the Internet.

Figure 2:
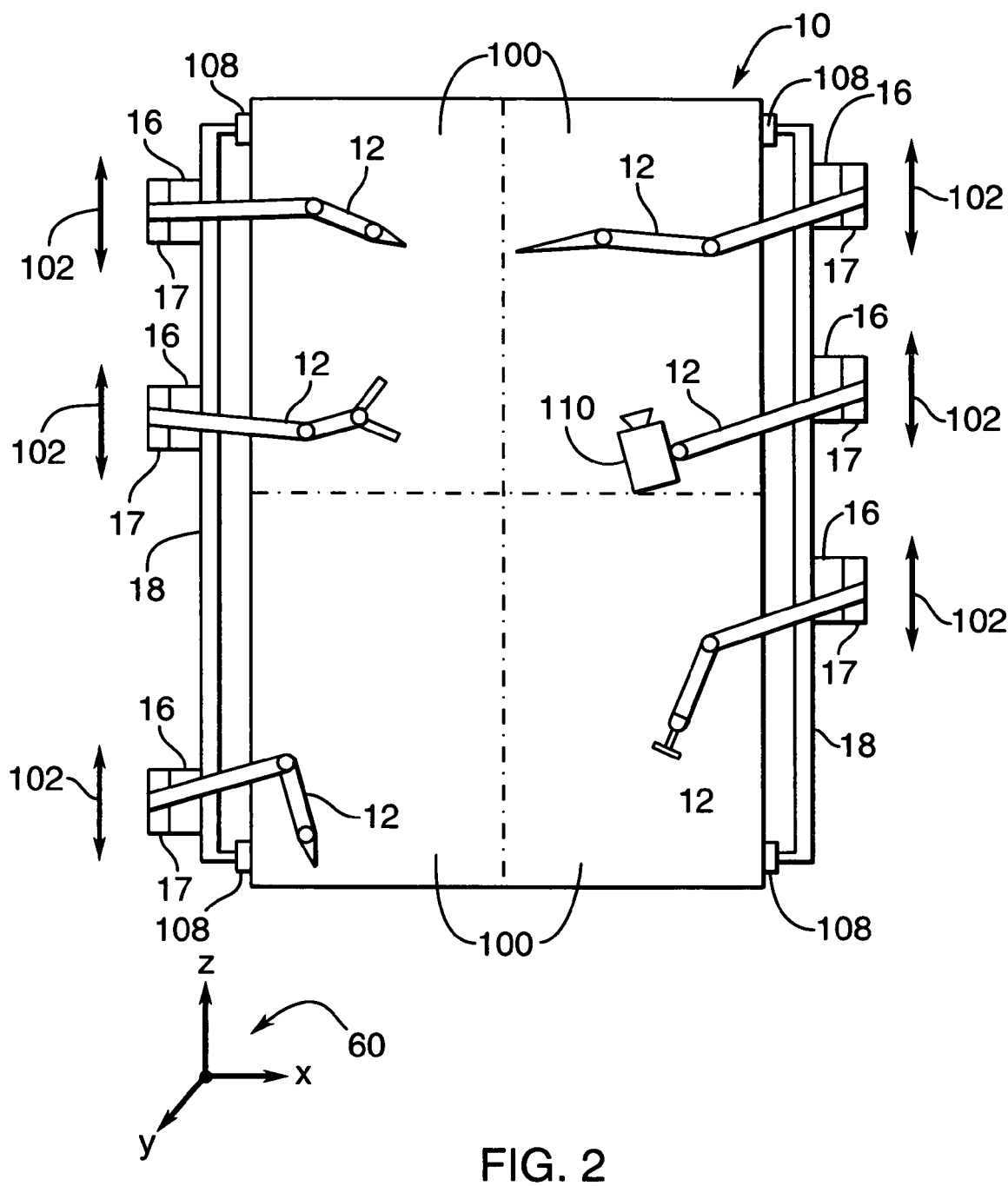
FIG. 2 shows a table of the robotic system of FIG. 1.

Referring to FIG. 2, an embodiment of the table 10 is shown having a number of quadrants 100 for positioning of the patient 24 (see FIG. 1) and the respective base stations 16 located along the track system 18. A secondary shoulder 17 can be attached to the proximal end of the arm 12 so as to facilitate connection to the desired base station 16, as further described below. The base stations 16 are configured to independently move or otherwise traverse (as identified by reference numeral 102) along the track system 18, so as to enable the console 20,34 to monitor or otherwise direct the placement of the attached arms 12 with respect to the desired quadrant 100 through position/orientation manager 204 (see FIG. 7). The base stations 16 can be releasably secured in selected positions along the track system 18, so as to provide a stable and secure base from which to operate the attached arms 12. Movement of the base stations 16 along the track system 18 can be done via motorized/actuated means, as is known in the art, or can be accomplished manually as desired. In either case (actuated or manual), sensors 106 (see FIG. 4) provide position/orientation information of the base stations 16 on the track system 18 as feedback to the manager 204, so as to help guide the operator 22 during surgery. The position sensors 106 also provide data to the controller computer 130 to facilitate automatic potential collision detection and avoidance between arms 12. The track system 18 can be affixed permanently to the table 10 by mounting connectors 108, so as to provide an integrated robotic system 112 (see FIG. 4) including the table 10, the track system 18, the base stations 16, the plug and play arms 12, operating system software 200, and a controller unit 35. A different example robotic system 112 configuration would have the track system 18, the base stations 16, the plug and play arms 12, and the controller unit 35 (for example) sold as a kit (e.g. a collection of robotic system 112 components for retrofitting to a table) for attachment to existing tables (not shown), such as OR tables (not shown) for military and/or other OR applications. In this case, the connectors 108 would be adaptable for connecting the track system 18 to the sides (for example) of the existing table so as to provide adequate support and stability for the connected base station 16—arm 12 pairs. In any case, the table 10 when connected to the track system 18 (and associated base stations 16 and arms 12) is considered part of the robotic system 112 for manipulation by the consoles 20,34.

Figure 3:
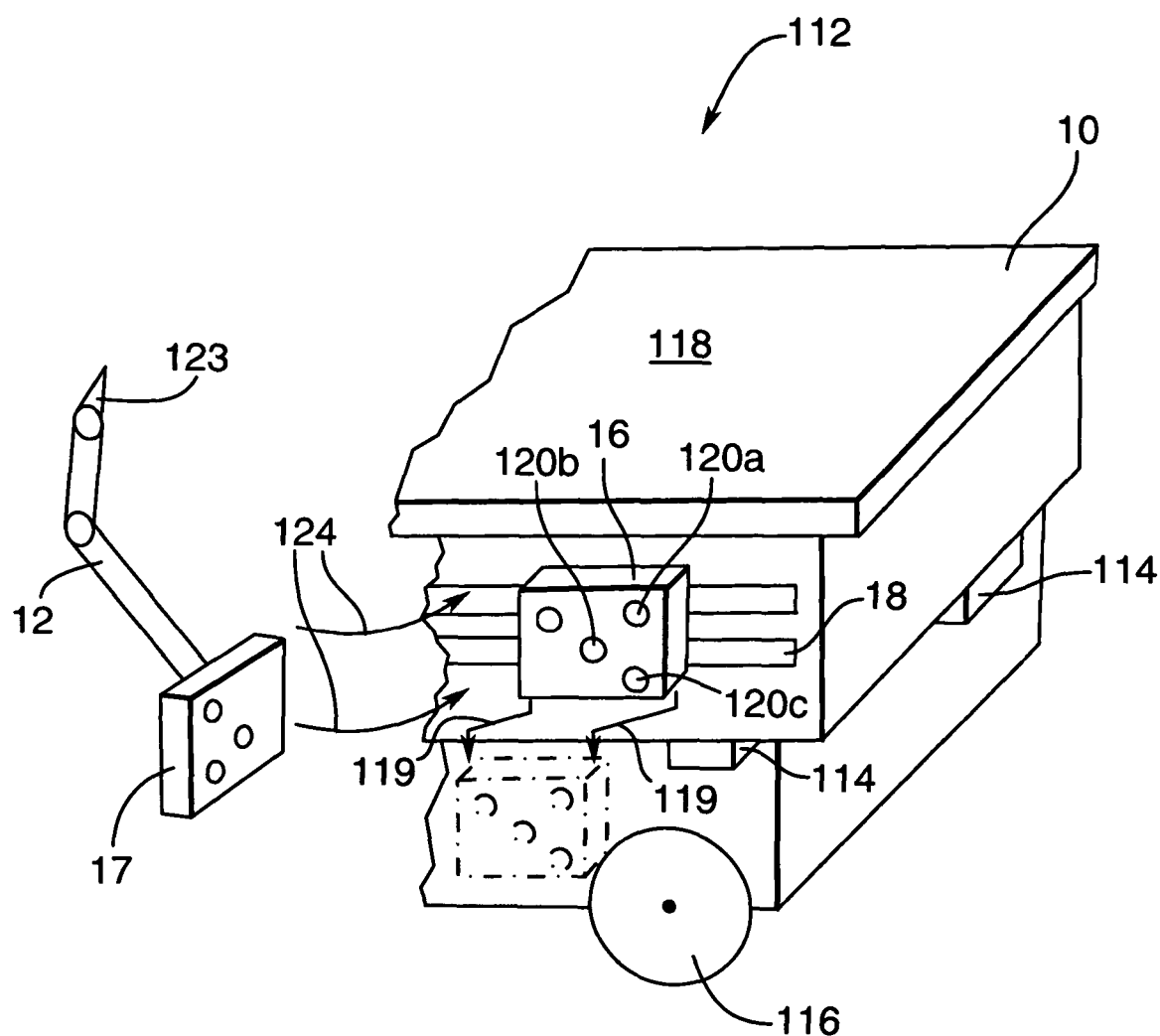
FIG. 3 shows a coupling between an arm and a base station of the system of FIG. 1.

Referring to FIG. 3, the robotic system 112 provides for repositioning/retraction (illustrated by reference numerals 119) of the base station 16 (shown physically repositioned in ghosted view) under the table 10, so as to facilitate a compact footprint for the table 10 when not in surgical use (e.g. when used in association with imaging equipment). It is also recognised that base stations 16 not in use during surgery could also be stored in retracted position. The table 10 can be mounted in the operating room 14 as a stationary operating facility or the table 10 can be equipped with, for example, wheels 116 to allow for relocation of the table 10. It is recognised in the case of using a mobile table 10 (e.g. with wheels 116) that wireless communication technologies and a suitable portable power supply would be used as needed for operation of the arms 12, base stations 16, and controller unit 35. Further, the table 10 can also have table actuators 114 to provide for automated positioning/orientation of the table top 118, such as but not limited to top 118 tilting and/or top 118 segmentation. In this case, the motion of the table actuators 114 can be tracked by the computer 314 using table position sensors 118 (see FIG. 4), such that the position/orientation information of the sensors 118 can be combined with the sensor 106 information of the base stations 16 and the position/orientation sensors (not shown) of the arms 12 to provide for position/orientation calculation of the distal ends of the arms 12 by the position/orientation manager 104. It is recognised that that the position/orientation of the surgical site of the patient 24 relative to the distal end of the arms 12 is also tracked as the table is positioned using additional body tracking sensors (not shown) as is known in the art. Accordingly, the relative position of the arms 12 (and portions thereof) with respect to other components of the robotic system 112, as well as with respect to the surgical site, can be tracked by the manager 204 using the sensors 106,118 and patient trackers (not shown), in view of the reference coordinate system 60. Further, the robotic system 112 allows for multi-arm 12 registration with respect to the patient 24 and medical images provided by the image guidance system 26 stored in an image data base 206 (see FIG. 7).

Referring again to FIG. 3, the base stations 16 have a data signal connector 120a for receiving/transmitting data to and from the arm 12 (e.g. camera signals, position sensor signals, etc . . . ), a control signal connector 120b for transmitting control signals (and receiving feedback signals) to actuated components of the arms 12 (e.g. motors, camera operation, ect . . . ), and a power supply connector 120c for supplying the requisite electrical and/or mechanical (e.g. pneumatic, hydraulic) power to actuated components of the arm 12 and tools 123. Complementary connectors of a data signal connector 121a, a control signal connector 121b and a power supply connector 121c are located in the secondary shoulder 17 for coupling (indicated by reference numeral 124) with those respective connectors 120a,b,c of the base station 16. It is recognised that data, control signal, and power requirements for arms 12 can vary depending upon the specific designed surgical task of the arm 12 (e.g. high voltage vs. low voltage, number of actuators, tool 123 operational requirements, etc . . . ), including the number of pins per connector 120a,b,c (e.g. 100-200 pins). Further, it is recognised that the physical dimensions, strength, weight, and stiffness of the base stations 16, secondary shoulders 17, and the connection there-between are designed to provide a stable base for operation of the attached arms 12. It is also recognised that unique mechanical and/or electrical configurations of the connectors 120a,b,c and 121a,b,c can help in auto-recognition of the arms 12 by the software 200 when attached to a selected one of the base stations 16. Control signalling is monitored by a control signal manager 208 (see FIG. 7). It is recognised that other connectors other than connectors 120a,b,c, 121a,b,c shown can be used as desired. Further, it is recognised that articulation can be provided between the shoulder 17 and adjacent base station 16 as well as between the arm 12 and the adjacent shoulder 17, as desired.

Referring again to FIGS. 1, 4 and 7, the arms 12 are in communication with a communication manager 202 of the consoles 20,34 via the communication capabilities 128 of the base stations 16. The base stations 16 can be linked through a wire based connection 28 to a wired communication link 30 of the console 20. It is recognized that the connection 28 and the link 30 are an existing operating room 14 communication infrastructure network 31 (see FIG. 2) such that the base stations 16 are attached to an electrical/mechanical connection harness 310 (see FIG. 4) located in the room 14 near the operating table 10. It is recognised that the connection 28 and link 30 can be fully compatible with IP fibre optic network protocols for connection to the remote consoles 20,34 for control of the robotic arms 12 via the base stations 16. Each of the base stations 16 and/or arms 12 can have assigned IP addresses to facilitate communication with the console 20,34 via the communication manager 202. For example, IP addresses may be assigned to arm controllers 320, 322, 328, 330 in the controller unit 35. The harness 310 can include switches and routers as is known in the art to enable communication with other telecommunication devices 38 connected to the room network 31. Examples of the network protocols can be such as but not limited to Ethernet/IP and TCP/IP, as further described below. Further, it is recognised that the harness 310 can be attached to a wireless unit 312 for sending and receiving wireless communications with the console 20,34 and other devices 38 via the network 31. Referring again to FIGS. 1 and 4, the base stations 16 are also in communication through the harness 310 (by wired connection 28 and/or wireless unit 312) to additional consoles 34 (Workstation #1 and workstation #2), as desired. These additional consoles 34 can be used for assistants 22 and/or remote tele-access by the surgeon 22 over a wide area network 37 (such as but not limited to the Internet) via the harness 310 and/or unit 312. It is recognised that each of the base stations 16 could have respective wireless units 312 rather than the shared unit 312 as shown via the harness 310. Concerning the wireless connections via the units 312, for example wireless data links can be used between the console 34 and the controller unit 35. Further, for example if wireless data links are to be used between the arms 12 on the table 10 and controller unit 35, at least arm motor drivers and power supplies would be located at the table 10 since they supply power to the motors, arm sensors and cameras.

The positioning of the robotic arms 12 as well the positions of the base stations 16 with respect to transport rails (on either side of the table 10) of the track system 18 are controlled/instructed by preferably two consoles 20,34 (e.g. workstation

1 and workstation #2). The consoles 20,34 are interlinked and can interchange the operational control of different sets of robotic arms 12 as well as base station 16 positioning along the track system 18. The table 10 can be made of a radiolucent material and could also be fully controllable as is known in the art (e.g. to effect desired positioning of the patient 24 thereon and the table 10 with respect to the surgeon 22—i.e. actuators 114) interchangeably by the two consoles 20,34. For example, the table 10 has the functionality of a regular OR (operating room) table 10 in terms of articulations for patient 24 positioning and restraint supports (not shown). The robotic arms 12 can be used with a full range of surgical instruments 123 and 3D cameras 110 as well as ultrasound and electrocautery instruments 123 attached to the end of the arms 12 (see FIG. 1). A data manager 1210 (see FIG. 7) processes the data signals in relation to the instruments 123, sensors 106, 118, camera 110, etc. . . .

The table 10 can use up to eight arms 12, for example, including two arms 12 for the primary surgeon 22 at workstation #1, two for assisting surgeon 22 at workstation #2, one for camera 110 placement and potentially one for retraction (not shown). It is recognised that the types of arms 12 attached to the base stations 16 could be changed to suit the type of surgical procedure such as but not limited to laparoscopic, orthopaedic, trauma, and microsurgery including neurosurgery and minimal access cardiac. It is recognized that the physical form/abilities and/or communications capability (with the base station 16) for each arm 12 can be different as suits the intended surgical procedure for each specific arm 12. The arms 12 and corresponding base stations 16 preferably would provide access to all parts of the patient 24 in a single surgical procedure performed by the surgeon 22, with selected access to each of the quadrants 100 (see FIG. 2) as required by the surgeon 22 during the surgical procedure, depending upon the particular selection of combined arms 12, controllers 320,322,328,330 (see FIG. 4), instruments 123, base stations 16 and their location on the track system 18, and console 20,34. This combination can be used to provide a dynamically configurable robotic system 112 suited to the planned surgical procedure on the patient 24. Configuration of the robotic system 112 (either automatic, semi-automatic, and/or manual) is facilitated by a configuration manager 212. It is recognised that one of the controllers 320,322,328,330 could be used to control more that one arm 12, as configured in the robotic system 112.

It is recognised that each arm 12 has a proximal end that is coupled to the base station 16 and a distal end for holding the surgical instruments 123. It is recognised that the arms 12 can be articulated multi-segmented manipulators and that the base stations 16 can be positioned independently of one another along the track system 18 according to the commands given by the consoles 20, 34. Further, articulation of each of the arms 12 can be done independently through assigned controllers 320,322,328,330 via the hand controllers 332 of the coupled console 20,34. Various portions of the arms 12 and the base stations 16 are tracked for position and/or orientation in the coordinate system, as reported to the consoles 20, 34 via the harness 310.

Figure 5:
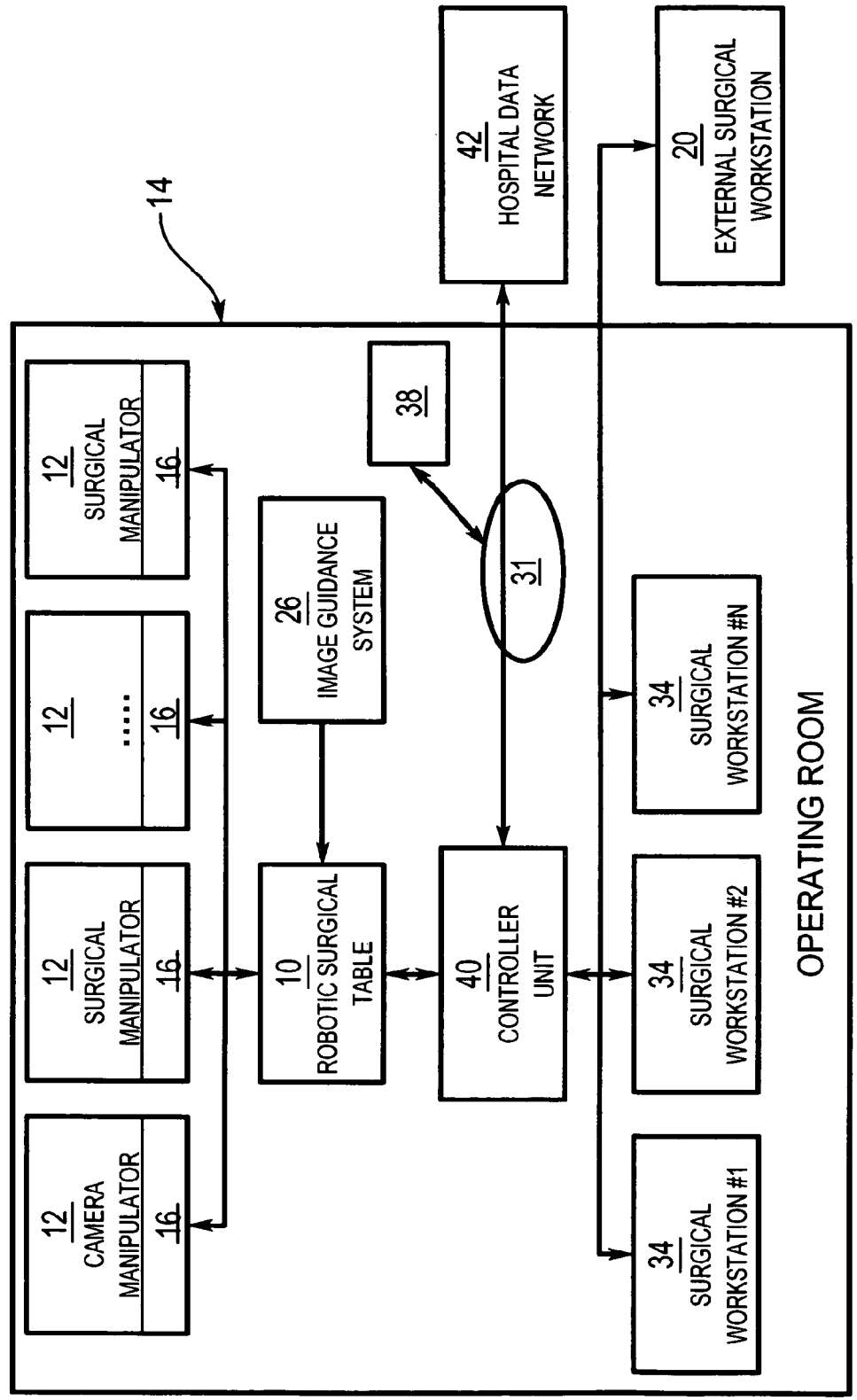
FIG. 5 is a further block diagram of the system of FIG. 1.

Referring to FIG. 5, the operating room 14 contains the table 10 with attached base stations 16. The arms 12 are attachable to the base stations 16 in a plug and play type connection that gives the users (e.g. surgeon 22 and assistant 22) the ability to plug the arms 12 into the base stations 16, such that operating software 200 on the computer 314 (see FIG. 4) of the consoles 20,34 recognizes that the utilised arm 12 is present, via a configuration manager 212 (see FIG. 7). For instance, if the camera 110 and associated arm 12 are connected to the base station 16 and are needed to provide intra-operative images to the consoles 20,34 via the configuration manager 212, a button could be pressed on the camera 110 and the camera 110 would send a "discover" request via the configuration manager 212 asking which consoles 20,34 are active on the network 31. The active console 20,34 would identify itself and send its location in the form of a universal resource locator (URL) back to the camera 110. Further, the transmission of the via the configuration manager 212 discover request could be sent automatically when the arm 12 is connected to the base station 16 or when the camera 110 is connected to the distal end of the arm 12.

Accordingly, the configuration manager 212 of the consoles 20,34 recognizes the arm 12 type, the appropriate respective electrical/mechanical and software configurations, and automatically applies the appropriate equipment and software for the recognised arm 12 operation, as programmed for the selected surgical procedure—i.e. one of the controllers 320,322,328,330 suitable for supporting operation of the recognised arm 12 (e.g. has suitable data signalling, control signalling, and power supply capabilities) is initialized by the robotic system 112 (either automatically, semi-automatically, and/or manually by surgeon 22 intervention). The initialization of the controllers 320,322,328,330 by the manager 212 can include such as but not limited to loading of appropriate drivers, configuration of power supply requirements, and loading of arm 12 operating software (for example including arm 12, joint, tool 123 control software, force sensor and configuration software) in the controller computer 130. The "plug and play" capability of the arms 12 may be implemented using the open, industry standard, Universal Plug and Play (UPnP), which uses Internet protocols for seamless device plug-in. The Universal Plug and Play capability is an example open industry standard that Microsoft™ promotes as seamless proximity networking that uses standardization on the network 31 rather than in devices using existing Internet standards.

The Universal Plug and Play (UPnP) protocol uses Internet and Web protocols via the configuration manager 202 to enable arms 12 and other devices 38, such as but not limited to PCs 20,34, peripherals, intelligent appliances, and wireless devices, to be plugged into the room network 31 and automatically recognise one another. With UPnP, when the user 22,32 plugs the arm 12 into the room network 31 via the base station 16, the arm 12 will be configured via the manager 212 (along with preferred configuration of the base station 16), acquire the predefined TCP/IP address, be associated with an appropriate controller 320,322,328,330, be assigned to respective controller(s) of the hand controller 332, and use a discovery protocol based on the Internet's Hypertext Transfer Protocol (HTTP), for example, to announce its presence on the room network 31 to other connected devices 38. Using the UpnP protocol, the arms 12 and other devices 38 can use Extensible Markup Language (XML) or another common language to communicate to each other through the network 31. The UpnP protocol facilitates seamless proximity networking of the arms 12 and other devices 31 coupled to the network 31 (as well as the network 37) to provide standardization on the network 31,37 rather than in the individual arms 12 and devices 38, using existing Internet standards as given by example above. It is recognized that the network communications can be desired and/or wireless based communications.

Figure 7:
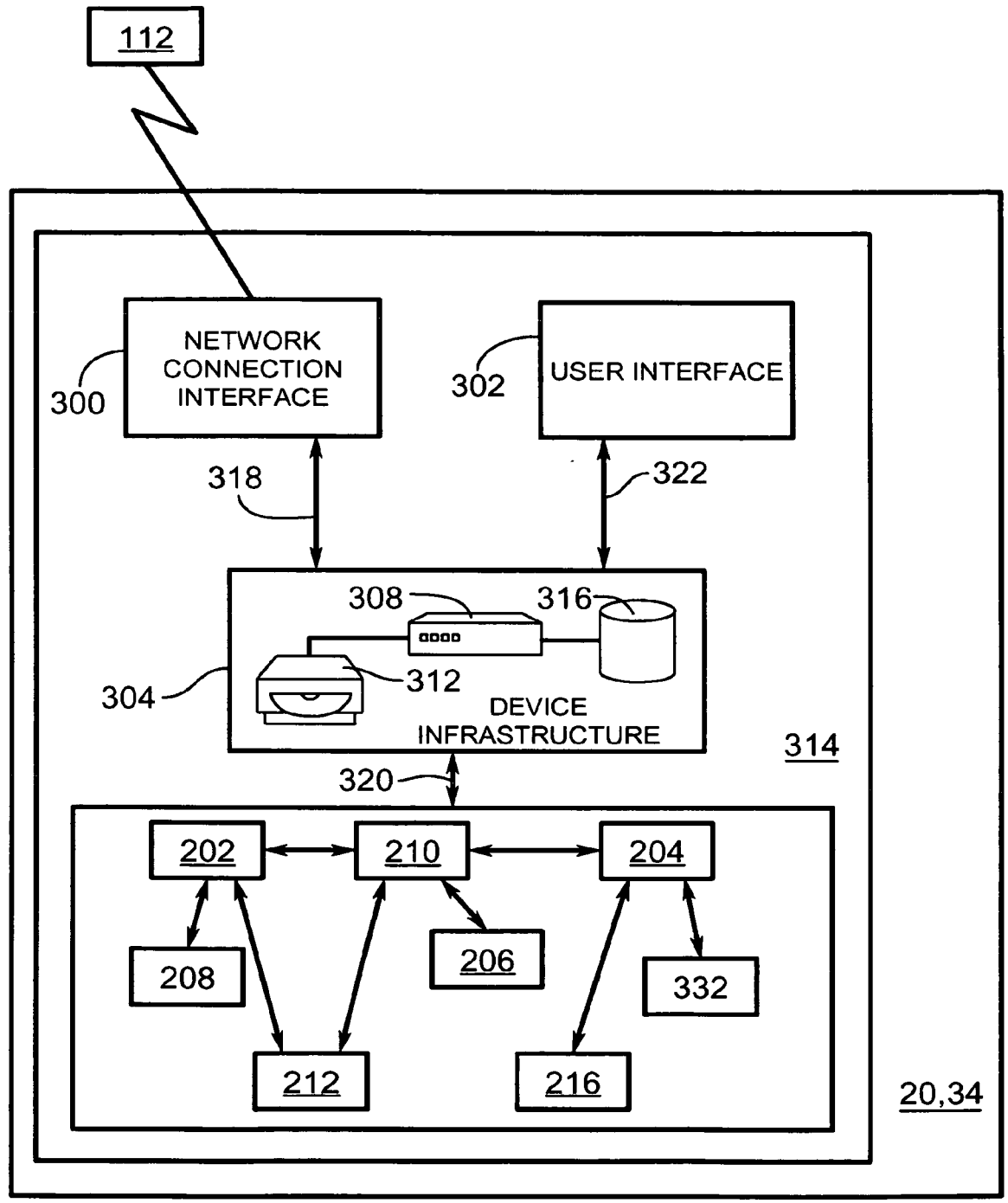
FIG. 7 is a functional block diagram of operating software of the system of FIG. 1.

Referring to FIG. 7, the computer 314 has software 200 for operating the robotic system 112. The computer 314 includes a network connection interface 300, such as a wireless transceiver or a wired network interface card or a modem, coupled via connection 318 to a device infrastructure 304. The connection interface 300 is connectable during operation of the console 20,34 to the network 104. The network 31,37 supports the transmission of data/signalling in network messages between consoles 20,34 and the robotic system 112. The consoles 20,34 also have a user interface 302 (including hand controllers 332), coupled to the device infrastructure 304 by connection 322, to interact with a user (e.g. surgeon 22). The user interface 302 includes one or more user input devices such as but not limited to a QWERTY keyboard, a keypad, a trackwheel, a stylus, a mouse, a microphone and the user output device such as an LCD screen display and/or a speaker. If the screen is touch sensitive, then the display can also be used as the user input device as controlled by the device infrastructure 304. The user interface 302 is employed by the user of the console 20,34 to coordinate the messages 105 over the network 31,37 for operation of the robotic system 112.

Referring again to FIG. 7, operation of the console 20,34 is enabled by the device infrastructure 304. The device infrastructure 304 includes a computer processor 308 and the associated memory module 316. The computer processor 308 manipulates the operation of the network interface 300 and the user interface 302 by executing related instructions, which are provided by an operating system and the software 200 (e.g. located in the memory module 316). Further, it is recognized that the device infrastructure 304 can include a computer readable storage medium 312 coupled to the processor 308 for providing instructions to the processor and/or to load/update the software 200 in the memory module 316. The computer readable medium 312 can include hardware and/or software such as, by way of example only, magnetic disks, magnetic tape, optically readable medium such as CD/DVD ROMS, and memory cards. In each case, the computer readable medium 312 may take the form of a small disk, floppy diskette, cassette, hard disk drive, solid state memory card, or RAM provided in the memory module 310. It should be noted that the above listed example computer readable mediums 312 can be used either alone or in combination.

Referring again to FIG. 7, the operating software 200 of the console 20,34 is shown, however it is recognised that the software 200, or portions thereof, could be installed and executed on the computer 130 of the controllers 320,322,328, 330. For example, the computers 130 could have any of the managers 202,204,208,210,212 installed and in communication with the software 200 of the computer 314, or functionality of the managers 202,204,208,210,212 could be shared between the computers 130,314 (i.e. in a distributed computing environment). Further, it is recognised that the software 200 of the computer 314 (for example via the configuration manager 212) could be operated to install relevant managers 202,204,208,210,212 (or portions thereof) as operating software of the computers 130.

Referring again to FIG. 7, the software 200 uses the user interface 302 for providing operator 22 input to the software 200 and associated managers 202,204,208,210,212,216. The communication manager 202 provides for communication of data signals to/from the data manager 210 and communication of control signals to/from the control manager 208. The database manager 210 provides for such as but not limited to persistence and access of image data to/from an image database 206, data related to the functioning/set-up of various elements of the robotic system 112 (e.g. arms 12, base station 16, controllers 320,322,328,330, actuators 114, and various position/orientation sensor data, and for providing data as needed to the position and orientation manager 204. The control manager 208, in cooperation with the hand controllers 332 and position/orientation information, provides for monitoring the operation of the arms 12, base stations 16, actuators 114, imaging equipment (e.g. camera 110), and tools 123. The position/orientation manager 204 is responsible for such as but not limited to receiving sensor data from the data manager 210 for calculating the position and orientation of the respective arm 12 components, tools 123, base stations 16, patient 24, and tabletop 118. The calculated position/orientation information is made available to such as but not limited to the actuation of the hand controllers 332, the display manager 216, and the control manager 208. The configuration manager 212 provides for such as but not limited to dynamic configuration of selected arms 12, base stations 16, controllers 320, 322,328,330, and the table top 118 comprising the desired robotic system 112 setup for a particular surgical procedure. The dynamic configuration can be automatic, semi-automatic, and/or manual operator 22 intervention. A display manager 216 of the software 200 coordinates/renders the calculated position/orientation information and the patient/tool images on the display 334 (see FIG. 4) of the user interface 302, as directed by the operator 22.

Referring again to FIG. 4, the consoles 20, 34 interact with a controller unit 35 to coordinate operation of the various arms 12 through the harness 310. The arms 12 are preferably lightweight components that are can be intuitively assembled with the base stations 16 using positive indication of connection correctness, such as, but not limited to color-coded and text labelled indicators. Further, the controller unit 35 can be operated by the operating software 200 of the consoles 20,34 to effect automatic instrument 123 and/or arm 12 placement to the last recorded position with respect to the table 10, as desired. Further, the surgeon's 22 personal preferences for system settings of the arms 12 and instruments 123, for such as but not limited to position, orientation, and arm/instrument operation settings can be recorded in the workstation memory 316 and can be used to configure the system of arms 12 and associated instruments 12 and base stations 16 via the configuration manager 212. The controller unit 35 can be connected to a hospital data network 42 (see FIG. 5) through the network 31. It is also recognised that the consoles 20,34 can have access to patient 24 image data through the hospital data network 42 and the image guidance system 26 for real time surgeries.

Referring again to FIG. 4, the controller unit 35 has a number of components 318 for controlling the arms 12 and base stations 16, such as but not limited to a camera controller 320, a tool changer 322, an arm locator 324, and surgical arm controllers 326 that can be connected through multiplexer units 328 through the harness 310. The controller unit 35 can also have base station 16 controllers 330 similar to the controllers 326 to coordinate the repositioning of the base stations 16 on the track system 18, as specified by the operating software of the consoles 20,34. The controllers 320,322,326, 330 include motor drivers, servo controllers, sensor processors and other control devices actuate the respective positioning hardware (e.g. motors) of the table 10, arms 12, and base stations 16, as is known in the art.

Figure 6:
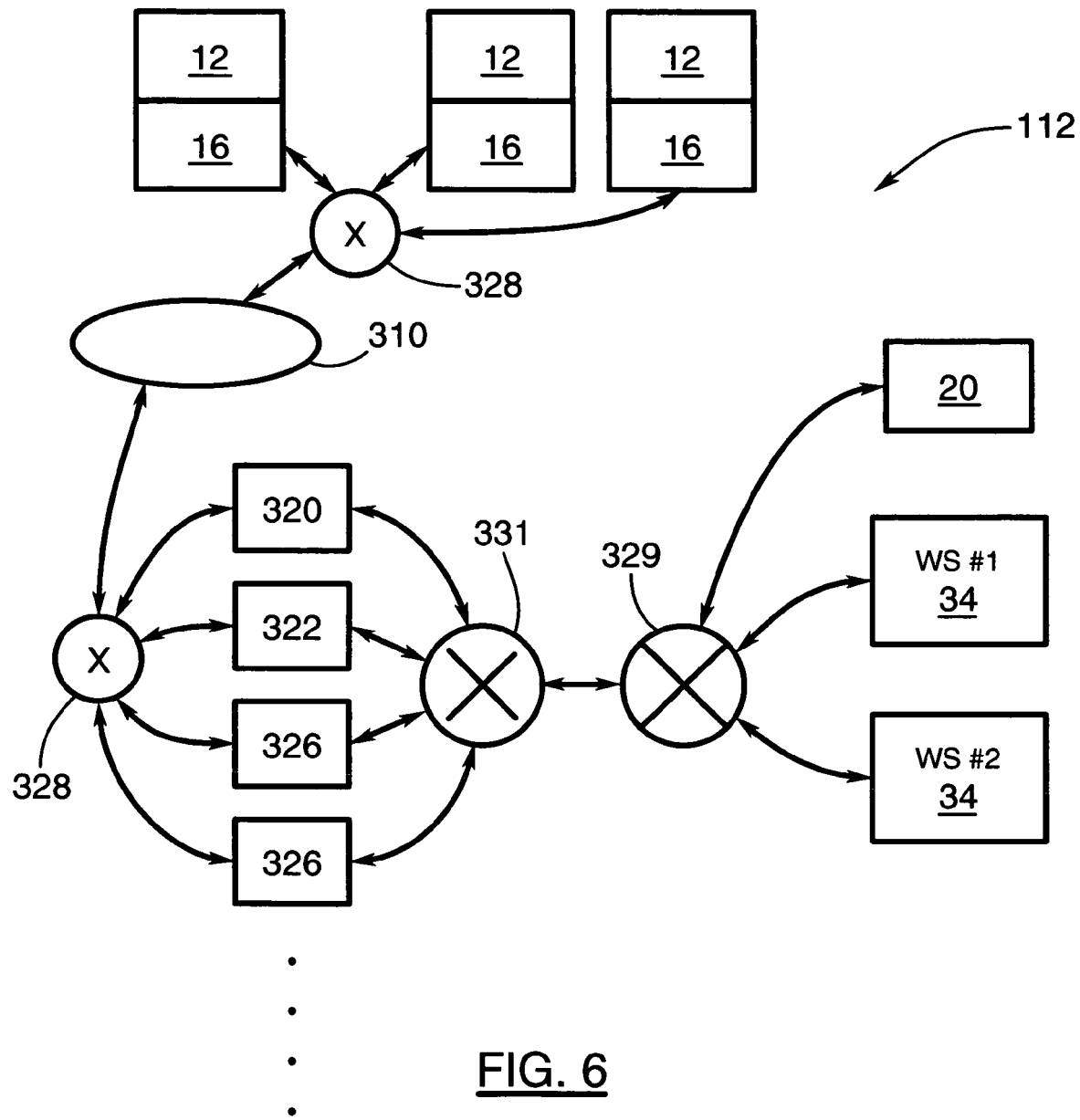
FIG. 6 shows dynamic configuration elements of the system of FIG. 4.

Referring to FIG. 6, operation of the respective arms 12 and associated base stations 16 is done through a multiplexed communication environment provided by the multiplexer units 328 coupling the various controllers 320,322,326,330 to the various base stations 16, arms 12, table positioning actuators 114, as dynamically configured via the configuration manager 212. Further, multiplexer units 331 and 329 are used to dynamically couple the consoles 20,34 with the controllers 320,322,326,330. Dynamic system redundancy and operator 22 flexibility are built into the robotic system 112 through use of the multiplexer units 328, 329, 331. For example, the multiplexer unit 329 provides for dynamically switching which console 20,34 is configured for real-time operation of the arms 12, such as the example case where the assistant 22 at console 12 must take over immediate control from the surgeon 22 (at console 20) of the arms 12 in use during surgery. In this case, the multiplexer 329 would dynamically switch the operational coupling from between the console 20 and the robotic system 112 to between the console 34 and the robotic system 112, using for example an override function of the software 200. It is also recognised that the multiplexer unit 329 could enable the dynamic configuration of both the console 20 and the console 34 for simultaneous operation of the arms 12, thus facilitating, for example, operational feedback of tactile (haptic) characteristics of the arms 12 (and associated tools 123) shared between the surgeon 22 and the assistant 22 (e.g. for training purposes). Through the simultaneous operation of both consoles 20,34 connected to the arm 12 operation, the surgeon 22 could demonstrate to the assistant 22 in a remote but real-time hands-on fashion the required force needed for a surgical technique, including example degree(s) of movement of console 34 controls (e.g. joy stick or other hand controllers 332).

Referring again to FIG. 6, the multiplexer units 328 provide for dynamic operational coupling of the controllers 320, 322,326,330 to selected respective arms 12 and base stations 16. This dynamic operational coupling can be configured by controller selection functions of the configuration manager 212, which would be used by surgeon 22/assistant 22 to select which controllers 320,322,326,330 would be used to control which arm 12/base station 16. For example, the surgery on the patient 24 could be planned using a pair of base stations 16 and respective arms 12 plugged into the base stations 16. In the event of a malfunction with one of the base stations 16 when in use, the respective arm could be disengaged from the defective base station 16, optionally the defective base station 16 could be folded under the table top 118 (see FIG. 3), and the respective arm 12 could be plugged into another one of the available base stations 16 connected to the track system 18. In this case the same or different controller 320,322,326,330 could be operatively coupled to the new base station 16 (by user or otherwise automatic configuration) and the surgery could continue. It is recognised that switching of base stations 16 would depend upon the configuration of the respective arm 12 and the compatibility/capabilities of the connectors 120a,b,c and connectors 121a,b,c (see FIG. 3). Further, it is recognised in the event of switching controllers 320,322,326,330, the new controller 320,322,326,330 should be configurable to support the respective base station 16 and/or arm 12 as needed. This support would include data signalling, control signalling, and power supply requirements as needed by the base station 16 and arm 12 pair. A further possibility would be to dynamically switch from a defective controller 320,322, 328,330 to a new controller 320,322,328,330 if needed during surgery, or to switch from an in-use but defective arm 12, base station 16, controller 320,322,328,330 combination to a standby arm 12, base station 16, controller 320,322,328,330 combination. It is recognised that the software 200 would be used to dynamically configure the selected controller 320, 322,326,330 as required.

The operating software 200 (of the consoles 20,34) is configured instruct the controller unit 35 to enable switching between pairs of arms 12, completed through software and/or hardware selectors. For example, the configuration attributes of one of the arms 12 can be transferred to another of the arms 12 in the case where the other arm 12 is closer and/or provides better access for the surgeon 22 to the surgical region of the patient 24. Another example is for transferring control of one of the arms 12 from the surgeon console 20 to the assistant console 34, thereby allowing the assistant 22 to use their respective hand controllers 332 to remotely operate the arm 12 previously controlled by the hand controllers 332 of the surgeon console 20. The hand controllers 332 control servo motors (not shown) associated with the robotic arms 12 for articulating the instruments 123 at the surgical site. During the operation, the hand controllers 332 provide mechanical articulation and control of a variety of surgical instruments 123, coupled to the robotic arms 12, that each perform various surgical functions for the surgeon 22. Other functional capabilities of the software 200 can include such as but not limited to enhancing the surgeon's 22 skills by: two arms 12 will be position controlled by independent handcontrollers 332 and a scale factor between the input and instrument 123 tip motion will be selectable within a specified range; removing unwanted tremor; providing desired 3D visualization on a display 334; and provide haptic feedback to the surgeon 22, as facilitated by the control manager 208 and the display manager 216. Further capabilities of the software 200 can include: pre-programmed activity of the planned surgery (i.e. surgical steps and required arms 12 and instruments 123 combinations); pre-programmed safety protocols for operating the arms 12 in the surgical environment; and necessary instruments 123 for the surgery as well as instruments 123 suitable for selected arm 12 types, as facilitated by the configuration manager 212. As well, sensors 336 can be connected to the network 31 so as to provide feedback to the surgeon of impending collision of the arms 12 and their instruments 123, as well as collision with any other tracked entities (not shown) in the room 14, as facilitated by the manager 204. Further, it is recognised that potential collision between respective base stations 16, between adjacent arms 12, and between the arms 12 and the patient 24 is monitored by the computer software 200 using the combined position/orientation sensor information of sensors associated with the table 10, arms 12, and base stations 16 of the robotic system 112.

For example, the software 200 can use the sensor signals to configure the consoles 20,34 to indicate to the surgeon 22 impending collision using audio, visual, and/or tactile feedback, as well as to restrict movements of the hand controllers 332 via the hand controller actuators 218 to inhibit movement of the arms 12 and associated instruments 123 into predefined no-go zones with respect to internal regions of the patient 24 and external regions of the room 14. In general, the software 200 will facilitate the control of the arms 12 and base stations 16 to perform of a variety of robotic surgeries in neurology, orthopedic surgery, general surgery, urology, cardiovascular and plastic surgery, for example. The software will also facilitate tele-robotic remote surgery by the surgeon 22 from a distance through the IP protocols over the networks 31, 37.

Due to the modular architecture of the robotic system 112, additional components 38 can be connected to the network 31 such as but not limited to: teaching add-ons like additional workstations and monitors; tele-mentoring—supervisory control from a second workstation; and visualization of additional image modalities such as ultrasonic or fluoroscopic of the imaging apparatus 26. Further, it is recognised that the track system 18 and table 10 with the harness 310 can be a single piece (surgical robot, operating bed) equipment which can reduce the set up time for robotic surgery. Attachable to the system are the base stations 16 and the arms 12 with instruments 123. It is recognised that the base stations 16 could be secured to the track system 18 to be somewhat less interchangable as compared to the arms 12. Also, the ability of the arms 12 to position and orient themselves with respect to the patient 24, under direction of the controller unit 35, can allow for multi-quadrant 100 surgery on the body of the patient 24. The control of the operating table 10 as well as the robotic arms 12 and base stations 16 (via the control unit 35 and consoles 20,34) gives the surgeon 22 control of the surgery, and the connectivity to remote consoles 20 make for tele-surgical access to experts via the network 37. The table 10 can be provided with base stations 16 attached or can be provided as adapted to connect with base stations 16 as decided subsequently by the purchaser of the table 10.

Figure 8:
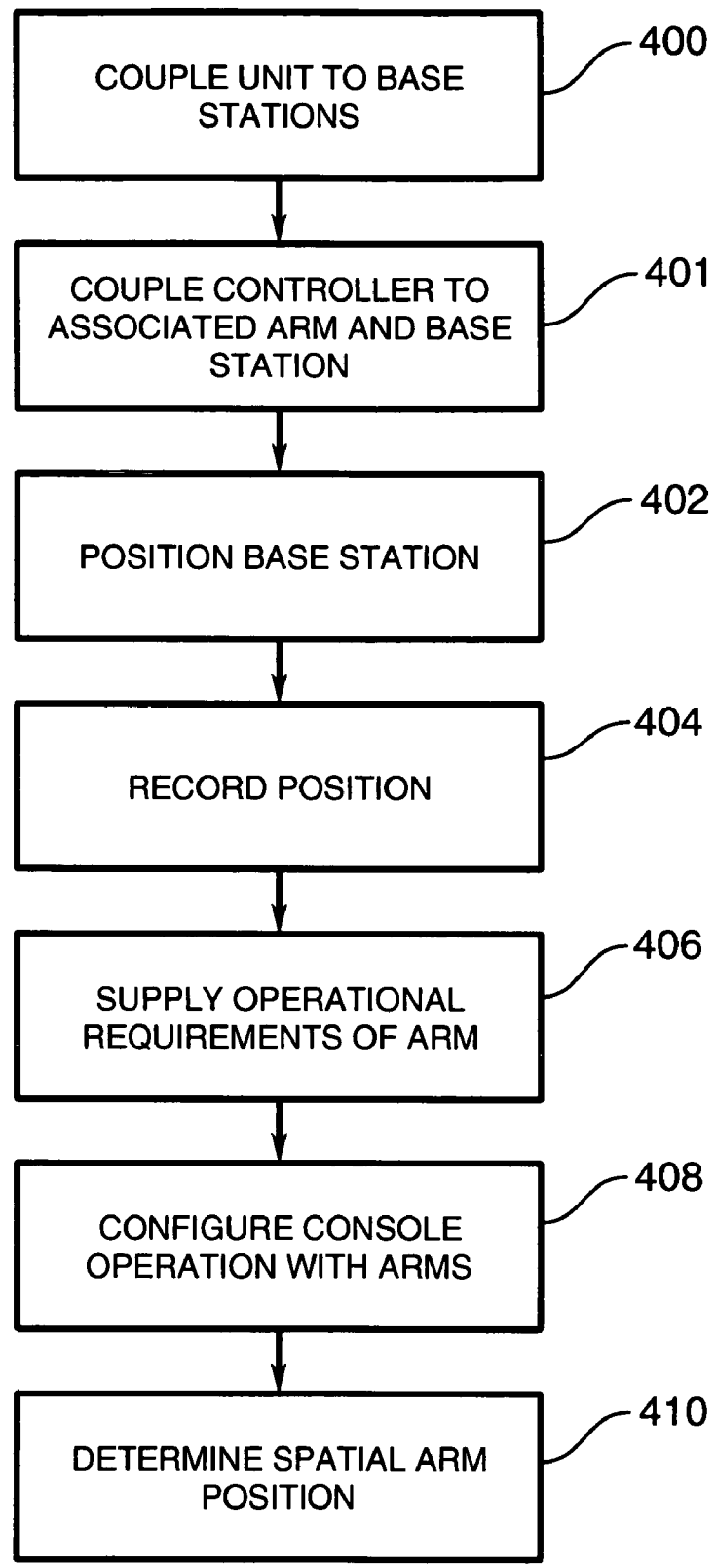
FIG. 8 is a flowchart of an example operation of the system of FIG. 1.

Referring to FIG. 8, an example operation of the robotic system 112 includes the steps of coupling 400 the control unit 35 to at least two selected base stations 16 of a plurality of the base stations 16 associated with the table 10, such that the control unit 35 dynamically connects operative remote control between the selected base stations 16 and at least one of the operator consoles 20,34. Step 401 is assigning a selected one of the robotic arms 12 to the selected base station 16, in combination with an assigned controller 320,322,328,330 of the controller unit 35 to the selected base station 16 for the purpose of assigning operative remote control of the selected robotic arm 16. Step 402 is to position the selected base stations 16 at locations on the track system 18. Step 404 is to record the position of each of the selected base stations 16 at the respective locations along the track system 18, such that this recorded position information of the base stations 16 can be used in position/orientation calculations of the attached arms 12 by the manager 204 (see FIG. 7). Step 406 is supplying power supply, control signalling, and data communication from the base station 16 to the respect attached robotic arm 12 through the connectors 120a,b,c and 121a,b,c, so as to assist the consoles 20,34 in monitoring placement of proximal ends of each of the selected robotic arms 12 at the respective locations about the patient 24 on the support table 10.

Step 408 is providing communication access between the controller unit 35 and the operator console 20 (or 34) and a different operator console 34 for the purpose of the sharing the assignment of operative remote control of the robotic arms 12. A further step 410 is determining the spatial position of the selected robotic arm 12 in the coordinate system 60 based on position sensor information related to the spatial positioning of the selected robotic arm 12, including: patient 24 position; patient support table 10 position; and position of the selected base station 16 along the track system 18 (the position sensor information can include orientation information where desired).

The Ethernet/IP (Ethernet Industrial Protocol) used on the network 37 is a network communication standard, implemented by the manager 202, capable of handling large amounts of data at example speeds of 10 Mbps or 100 Mbps, and at up to 1500 bytes per packet. The specification uses an open protocol at the Application layer and is applicable for control applications of the robotic arms 12 and base stations 16. Ethernet/IP typically employs active star network technology. It allows mixing of 10 Mbps and 100 Mbps products, for example, and is compatible with most Ethernet switches. Ethernet/IP is used with personal computers, mainframes, robots, input/output (I/O) devices and adapters, programmable logic controllers (PLCs), and other devices. The specification is supported by the Industrial Ethernet Association (IEA), ControlNet International (CI), and the Open DeviceNet Vendor Association (ODVA).

TCP/IP (Transmission Control Protocol/Internet Protocol) is the basic communication language or protocol of the Internet 37. It can also be used as a communications protocol in a private network 31 (either an intranet or an extranet). TCP/IP is a two-layer program. The higher layer, Transmission Control Protocol, manages the assembling of a message or file into smaller packets that are transmitted over the Internet 37 and received by a TCP layer that reassembles the packets into the original message. The lower layer, Internet Protocol, handles the address part of each packet so that it gets to the right destination, i.e. the consoles 20,34 and the controller unit 35 for the arms 12 and base stations 16. Each gateway computer (not shown) on the network 31 checks this address to see where to forward the message. Even though some packets from the same message are routed differently than others, they are reassembled at the destination.

TCP/IP uses the client/server model of communication in which the console 20,32 requests and is provided a service by another device 38 in the network 31,37. TCP/IP communication is primarily point-to-point, meaning each communication is from one point (or host computer) in the network 31,37 to another point or host computer. TCP/IP and the higher-level applications that use it are collectively said to be "stateless" because each client request is considered a new request unrelated to any previous one (unlike ordinary phone conversations that require a dedicated connection for the call duration). Being stateless frees network paths so that everyone can use them continuously. (Note that the TCP layer itself is not stateless as far as any one message is concerned. Its connection remains in place until all packets in a message have been received.)

TCP/IP includes protocols such as the World Wide Web's Hypertext Transfer Protocol (HTTP), the File Transfer Protocol (FTP), Telnet (Telnet) which lets you logon to remote computers, and the Simple Mail Transfer Protocol (SMTP). These and other protocols are often packaged together with TCP/IP as a "suite." Personal computer users usually get to the Internet 37 through the Serial Line Internet Protocol (SLIP) or the Point-to-Point Protocol (PPP). These protocols encapsulate the IP packets so that they can be sent over a dial-up phone connection to an access provider's modem. Protocols related to TCP/IP include the User Datagram Protocol (UDP), which is used instead of TCP for special purposes. Other protocols are used by network host computers for exchanging router information. These include the Internet Control Message Protocol (ICMP), the Interior Gateway Protocol (IGP), the Exterior Gateway Protocol (EGP), and the Border Gateway Protocol (BGP).

It is recognised that some or all of the above described software 200 functionality could be provided by suitable hardware based modules (not shown), as desired.

The Embodiments of the invention in which an exclusive property or privilege is claimed are defined as the follows:

1. A robotic surgical system for performing a surgical procedure, comprising:
   a robotic arm removably coupled to a base station that is removably mounted to a track and having motorized movement along the track, the track connected to and around a periphery of a patient support table around a plane defined by the patient support table, the robotic arm having a surgical instrument connected thereto for performing the surgical procedure;
   an operator console in communication with the base station and the robotic arm coupled thereto, the operator console configured to:
   (a) receive a command regarding the surgical procedure to be performed by the surgical instrument at a surgical site;
   (b) calculate a base station position along the track based on a received current base station position, the surgical site and the surgical procedure;

(c) provide automated control to the motor to re-position the base station to the calculated base station position; and (d) position the robotic arm so that the surgical instrument is positioned at the surgical site based on the calculated base station position, the surgical site, the surgical procedure and a current position of the surgical instrument;

wherein the operator console additionally receives a user input to manipulate the surgical instrument at the surgical site to perform the surgical procedure.

2. The system of claim 1, wherein the new base station position is additionally calculated based on the position of a patient on the patient support table.

3. The system of claim 2, wherein the position of the robotic arm is additionally based on the tilt of the patient support table.

4. The system of claim 3, wherein the current base station position, the current position of the surgical instrument, the position of the patient and the tilt of the patient support table are provided by a plurality of sensors.

5. The system of claim 4, wherein the patient support table is positionable within an imaging system.

6. The system of claim 5, wherein the operator console comprises a display capable of displaying a medical image of a patient and the system is further capable of performing real-time image guided surgery when positioned within an imaging system.

7. The system of claim 6 wherein the imaging system is a CT imaging system, a fluoroscopy imaging system or an MRI imaging system.

8. The system of claim 4, wherein the operator console is further configured to recognize the robotic arm and retrieve an operation configuration for the robotic arm to the operator console to control the robotic arm upon connection of the robotic arm to the base station.

9. The system of claim 4, wherein the command regarding the surgical procedure is pre-planned and stored by the operator console prior to commencing the surgical procedure.

10. The system of claim 4, further comprising a further robotic arm removably coupled to a further base station, the further base station removable coupled to the track.

11. The system of claim 10, further comprising a second operator console and a multiplexer unit for coupling between the first operator console and the second operator console, the multiplexer unit permitting communication between any one of the operator consoles and any one of the base stations and the robotic arms removably coupled thereto.

12. The system of claim 11, wherein the multiplexer unit permits simultaneous communication between the operator consoles and each base station and the robotic arms connected thereto, wherein each robotic arm can be independently controlled by each respective operator console.

13. The system of claim 10, wherein the operator console is further configured to generate an impending collision notification based on the current base station position of the base station, a current robot position of the robotic arm removably coupled thereto, a current further base station position of the further base station and a current further robot position of the further robotic arm coupled thereto.

14. The system of claim 13, wherein the impending collision notification generated is a haptic feedback.

15. The system of claim 14, wherein the operator console is further configured to prevent additional movement of the robotic arm in response to the impending collision feedback notification in the direction of impending collision.

16. A method for operating a robotic surgical system for a surgical procedure, the method comprising:

(a) receiving a command regarding a surgical procedure to be performed by a surgical instrument at a surgical site, the surgical instrument connected to a robotic arm removably coupled to a base station;

(b) calculating a new base station position along a track removably coupled thereto based on a received current base station position, the surgical site and the surgical procedure, the track connected to and around a periphery of a patient support table around a plane defined by the patient support table;

(c) providing automated control to the base station to re-position the base station to the calculated new base station position;

(d) positioning the robotic arm so that the surgical instrument is positioned at the surgical site based on the calculated base station position, the surgical site, the surgical procedure and the current position of the surgical instrument; and (e) receiving a user input to manipulate the surgical instrument at the surgical site to perform the surgical procedure.

17. The method of claim 16, wherein the new base station position is additionally calculated based on the position of a patient on the patient support table.

18. The method of claim 17, wherein the positioning of the robotic arm is additionally based on the tilt of the patient support table.

19. The method of claim 18, wherein the current base station position, the current position of the surgical instrument, the position of the patient and the tilt of the patient support table are provided by a plurality of sensors.

20. The method of claim 19, further comprising positioning the patient support table within an imaging system.

21. The method of claim 20, further comprising displaying a medical image generated by the imaging system of a patient and the surgical procedure is an image guided surgery.

22. The method of claim 21, wherein the medical image is a CT image, a fluoroscopy image or an MRI image.

23. The method of claim 19, further comprising recognizing the robotic arm and retrieving an operation configuration for the robotic arm upon connection of the robotic arm to the base station.

24. The method of claim 19, wherein the command regarding the surgical procedure is pre-planned and stored prior to commencing the surgical procedure.

25. The method of claim 19, further comprising generating an impending collision notification based on the current base station position of the base station and a current robotic arm position of the robotic arm removably coupled thereto.

26. The method of claim 25, wherein the impending collision notification is a haptic feedback.

27. The method of claim 26, further comprising preventing additional movement of the robotic arm in response to the impending collision notification in the direction of impending collision.

* * * * *